US00PP23487P2

(12) United States Plant Patent
Beekenkamp

(10) Patent No.: US PP23,487 P2
(45) Date of Patent: Mar. 19, 2013

(54) ***DAHLIA* PLANT NAMED 'BKDAOR'**

(50) Latin Name: *Dahlia hybrida*
Varietal Denomination: Bkdaor

(75) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 93 days.

(21) Appl. No.: 13/068,694

(22) Filed: May 17, 2011

(51) Int. Cl.
*A01H 5/00* (2006.01)

(52) U.S. Cl. ..... Plt./321

(58) Field of Classification Search ..... Plt./321
See application file for complete search history.

*Primary Examiner* — June Hwu
(74) *Attorney, Agent, or Firm* — C. A. Whealy

(57) ABSTRACT

A new and distinct cultivar of *Dahlia* plant named 'Bkdaor', characterized by its compact, upright, somewhat outwardly spreading and mounding plant habit; dense and bushy growth habit; early and continuous flowering habit; double inflorescences with yellow to yellow orange-colored ray florets; and good garden performance.

2 Drawing Sheets

Botanical designation: *Dahlia hybrida.*
Cultivar denomination: 'BKDAOR'.

BACKGROUND OF THE INVENTION

The present invention relates to a new and distinct cultivar of *Dahlia* plant, botanically known as *Dahlia hybrida*, and hereinafter referred to by the name 'Bkdaor'.

The new *Dahlia* plant is a product of a planned breeding program conducted by the Inventor in Maasdijk, The Netherlands. The objective of the breeding program is to create new container *Dahlia* plants that have a freely branching habit, attractive ray floret coloration, long flowering period and good garden performance.

The new *Dahlia* plant originated from an open-pollination in July, 2006 in Maasdijk, The Netherlands of a proprietary selection of *Dahlia hybrida* identified as code number 2006-0136, not patented, as the female, or seed, parent with an unknown selection of *Dahlia hybrida* as the male, or pollen, parent. The new *Dahlia* plant was discovered and selected by the Inventor as a single flowering plant from within the progeny of the stated open-pollination in a controlled environment in Maasdijk, The Netherlands in July, 2007.

Asexual reproduction of the new *Dahlia* plant by cuttings in a controlled environment in Maasdijk, The Netherlands since November, 2007 has shown that the unique features of this new *Dahlia* plant are stable and reproduced true to type in successive generations.

SUMMARY OF THE INVENTION

Plants of the new *Dahlia* have not been observed under all possible environmental conditions and cultural conditions. The phenotype may vary somewhat with variations in environment such as temperature and light intensity, without, however, any variance in genotype.

The following traits have been repeatedly observed and are determined to be the unique characteristics of 'Bkdaor'. These characteristics in combination distinguish 'Bkdaor' as a new and distinct *Dahlia* plant:

1. Compact, upright, somewhat outwardly spreading and mounding plant habit.

2. Dense and bushy growth habit.
3. Early and continuous flowering habit.
4. Double inflorescences with yellow to yellow orange-colored ray florets.
5. Good garden performance.

Compared to plants of the female parent selection, plants of the new *Dahlia* differ primarily in the following characteristics:

1. Plants of the new *Dahlia* are taller than plants of the female parent selection.
2. Leaves of plants of the new *Dahlia* are lighter green in color than leaves of plants of the female parent selection.
3. Plants of the new *Dahlia* and the female parent selection differ in ray floret color as plants of the female parent selection have light orange-colored ray florets.

Plants of the new *Dahlia* can be compared to plants of *Dahlia* 'Gallery Vincent', disclosed in U.S. Plant Pat. No. 10,500. In side-by-side comparisons conducted in Maasdijk, The Netherlands, plants of the new *Dahlia* differed from plants of 'Gallery Vincent' in the following characteristics:

1. Plants of the new *Dahlia* were more compact than plants of 'Gallery Vincent'.
2. Leaves of plants of the new *Dahlia* were lighter green in color than leaves of plants of 'Gallery Vincent'.
3. Plants of the new *Dahlia* had shorter peduncles than plants of 'Gallery Vincent'.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of a typical flowering plant of 'Bkdaor' grown in a container.

The photograph on the second sheet is a close-up view of a typical inflorescence of 'Bkdaor'.

DETAILED BOTANICAL DESCRIPTION

The aforementioned photographs and the following observations and measurements describe plants grown during the winter in 15-cm containers in a glass-covered greenhouse in Maasdijk, The Netherlands and under conditions and practices which approximate those generally used in commercial container *Dahlia* production. During the production of the plants, day and night temperatures ranged from 17° C. to 19° C. Plants were pinched one time and were nine weeks old when the photographs and description were taken. In the following description, color references are made to The Royal Horticultural Society Colour Chart, 2007 Edition, except where general terms of ordinary dictionary significance are used.

Botanical classification: *Dahlia hybrida* 'Bkdaor'.

Parentage:

*Female, or seed, parent*.—Proprietary selection of *Dahlia hybrida* identified as code number 2006-0136, not patented.

*Male, or pollen, parent*.—Unknown selection of *Dahlia hybrida*, not patented.

Propagation:

*Type*.—By cuttings.

*Time to initiate roots, summer*.—About 16 days at temperatures of about 18° C. to 21° C.

*Time to initiate roots, winter*.—About 19 days at temperatures of about 19° C. to 21° C.

*Time to produce a rooted young plant, summer*.—About 21 days at temperatures of about 18° C. to 21° C.

*Time to produce a rooted young plant, winter*.—About 23 days at temperatures of about 19° C. to 21° C.

*Root description*.—Medium in thickness, fibrous, white in color; tuber development has not been observed.

*Rooting habit*.—Moderate branching; medium density.

Plant description:

*Plant form and growth habit*.—Compact, upright, somewhat outwardly spreading and mounding plant form; broad inverted triangle; about seven primary lateral branches develop, each primary lateral branch with numerous secondary branches; inflorescences held above the foliar plane on strong peduncles; bushy and dense growth habit.

*Plant height*.—About 26.7 cm.

*Plant diameter or spread*.—About 30.3 cm.

*Lateral branches*.—Length: About 10.5 cm. Diameter: About 7 mm. Internode length: About 4 cm. Aspect: About 25° from vertical. Strength: Strong. Texture: Smooth, glabrous. Color: Close to 143C.

Foliage description:

*Arrangement*.—Leaves opposite; leaves either single or compound with three leaflets.

*Single leaves*.—Length: About 9.6 cm. Width: About 6.3 cm.

*Compound leaves*.—Length: About 16.2 cm. Width: About 14.9 cm.

*Leaflet leaves*.—Length: About 9.1 cm. Width: About 6 cm.

*Shape, single leaves and leaflets*.—Ovate.

*Apex, single leaves and leaflets*.—Apiculate.

*Base, single leaves and leaflets*.—Attenuate.

*Margin, single leaves and leaflets*.—Coarsely dentate.

*Venation pattern, single leaves and leaflets*.—Pinnate.

*Texture, upper surface, single leaves and leaflets*.—Smooth, glabrous; mid-vein, sparsely pubescent.

*Texture, lower surface, single leaves and leaflets*.—Smooth, glabrous.

*Color*.—Developing leaves and leaflets, upper surface: Close to N137C. Developing leaves and leaflets, lower surface: Close to 147B. Fully expanded leaves and leaflets, upper surface: Between N137A and 147A; venation, close to 144A. Fully expanded leaves and leaflets, lower surface: Close to 191A; venation, close to 144B.

*Petioles*.—Length: About 2.5 cm. Diameter: About 3.5 mm. Texture, upper and lower surfaces: Smooth, glabrous. Color, upper surface: Close to 144B. Color, lower surface: Close to 143C.

Inflorescence description:

*Appearance and arrangement*.—Double inflorescence form with ray and disc florets forming acropetally on a receptacle; inflorescences positioned above the foliar plane on strong peduncles; inflorescences face mostly upright; freely flowering habit, about 35 inflorescences developing per plant.

*Fragrance*.—None detected.

*Time to flower*.—Early flowering habit, plants begin flowering about ten weeks after planting; plants flower continuously during the late summer in The Netherlands.

*Post-production longevity*.—Inflorescences maintain good substance for about two to three weeks on the plant; inflorescences not persistent.

*Inflorescence bud*.—Height: About 1.4 cm. Diameter: About 1.6 cm. Shape: Flattened globular. Color: Close to 154A to 154B; towards the base, close to 143B to 143C.

*Inflorescence size*.—Diameter: About 9.1 cm. Depth (height): About 7 cm. Disc diameter: About 1.8 cm. Receptacle height: About 2 mm. Receptacle diameter: About 5 mm. Receptacle color: Close to 145C.

*Ray florets*.—Quantity per inflorescence: About 80 arranged in about four whorls. Length: About 3.9 cm. Width: About 2.4 cm. Shape: Obovate. Apex: Broadly acute. Base: Cuneate. Margin: Entire. Aspect: About 70° from vertical; ray florets concave. Texture, upper and lower surfaces: Smooth, glabrous; moderately velvety. Color: When opening, upper surface: Upper half, between 12A and 13A; lower half, between 14B and 21B. When opening, lower surface: Close to 15B to 15C; central band, close to 8A. Fully opened, upper surface: Between 1A and 2B; color becoming closer to between 22A and 23B with development. Fully opened, lower surface: Between 1A to 2B; towards the apex, close to N25C; color becoming closer to 23B; central band, close to 30B to 30C.

*Disc florets*.—Quantity per inflorescence: About 40. Length: About 1.6 cm. Diameter: About 3 mm. Shape: Tubular, elongated; apices, acute. Texture, inner and outer surfaces: Smooth, glabrous. Color, when opening and fully opened, inner and outer surfaces: Close to 14A; towards the base, close to 151C to 151D.

*Phyllaries*.—Quantity per inflorescence: About eight arranged in a single whorl. Length: About 1.7 cm. Width: About 5 mm. Shape: Narrowly oblong. Apex: Obtuse. Base: Broadly cuneate. Margin: Entire. Texture, upper and lower surfaces: Smooth, glabrous.

Color, upper and lower surfaces: Close to 150B; towards the base, close to 143B.

*Peduncles*.—Length, terminal peduncle: About 9.8 cm. Length, axillary peduncle: About 8.4 cm. Diameter: About 3.5 mm. Aspect: Erect to about 20° from vertical. Strength: Strong. Texture: Smooth, glabrous. Color: Close to 144A to 144B.

*Reproductive organs*.—Androecium, present on disc florets only: Quantity per floret: About five. Filament length: About 3 mm. Filament color: Close to 151C to 151D. Anther shape: Narrowly oblong. Anther length: About 3 mm. Anther color: Close to 22A. Pollen amount: Moderate. Pollen color: Close to 24A. Gynoecium, present on ray and disc florets: Quantity per floret: One. Pistil length: About 1.2 cm. Style length: About 9 mm. Style color: Close to 151C to 151D. Stigma shape: Cleft. Stigma color: Close to 22A. Ovary color: Close to 145C. Seeds/fruits: Seed and fruit development have not been observed on plants of the new *Dahlia*.

Disease/pest resistance: Plants of the new *Dahlia* have not been shown to be resistant to pathogens and pests common to *Dahlia*.

Garden performance: Plants of the new *Dahlia* have been observed to have good garden performance and to tolerate wind and rain. Plants of the new *Dahlia* have been observed to be tolerant to high temperatures of 35° C. and hardy to USDA Hardiness Zone 8.

It is claimed:

1. A new and distinct *Dahlia* plant named 'Bkdaor' as illustrated and described.

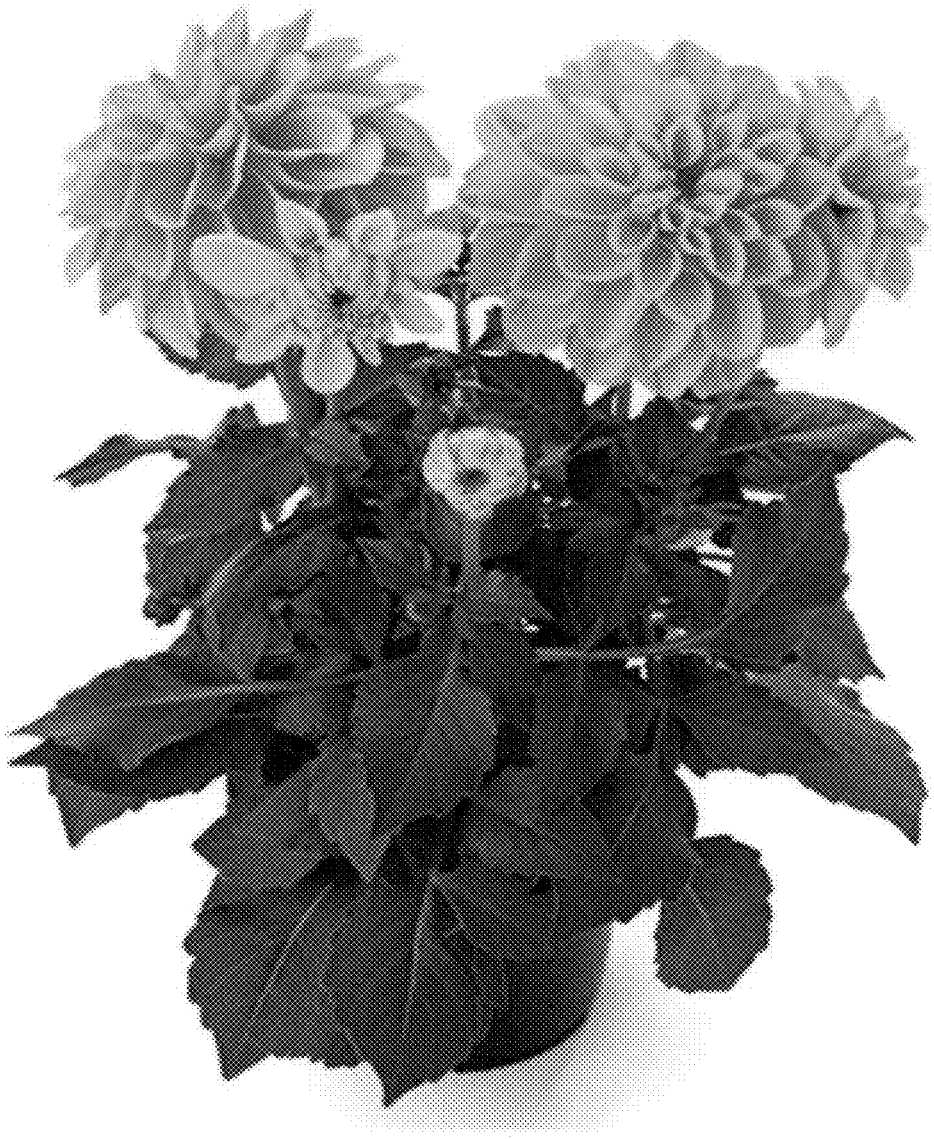

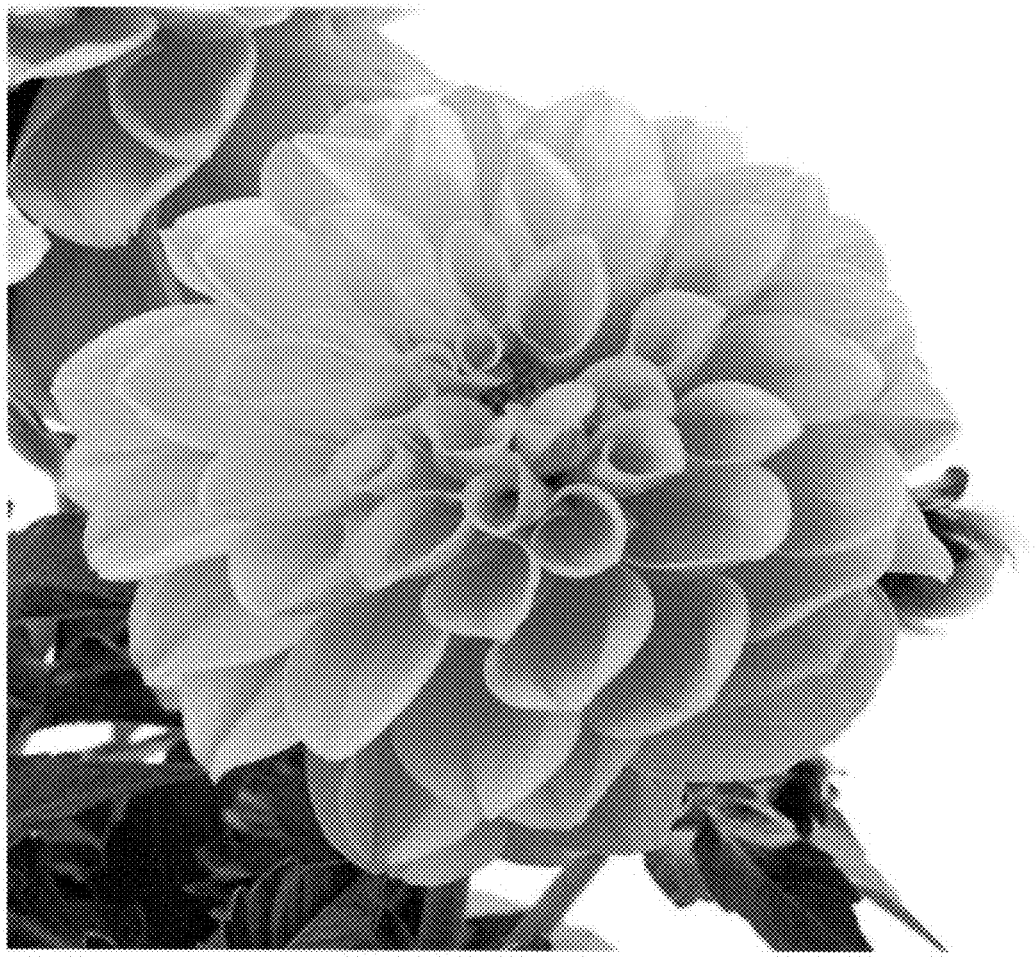

* * * * *